(12) United States Patent
Arstad et al.

(10) Patent No.: US 8,679,455 B2
(45) Date of Patent: *Mar. 25, 2014

(54) RADIOLABELLING METHODS

(75) Inventors: Erik Arstad, London (GB); Matthias Eberhard Glaser, Amersham (GB)

(73) Assignee: Hammersmith Imanet Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/158,555

(22) Filed: Jun. 13, 2011

(65) Prior Publication Data

US 2011/0236311 A1    Sep. 29, 2011

Related U.S. Application Data

(62) Division of application No. 11/721,694, filed as application No. PCT/GB2005/004729 on Dec. 9, 2005, now Pat. No. 7,972,588.

(30) Foreign Application Priority Data

Dec. 22, 2004 (GB) .................................. 0428012.9

(51) Int. Cl.
*A61K 51/00* (2006.01)
*A61M 36/14* (2006.01)

(52) U.S. Cl.
USPC .......... 424/1.69; 424/1.11; 424/1.65; 514/1.1

(58) Field of Classification Search
USPC ........... 424/1.11, 1.49, 1.65, 1.69, 1.73, 1.81, 424/1.85, 1.89, 9.1, 9.3, 9.4, 9.5, 9.6, 9.7, 424/9.8; 514/1, 1.1; 534/7, 10–16; 548/255
See application file for complete search history.

(56) References Cited

U.S. PATENT DOCUMENTS

| | | | |
|---|---|---|---|
| 4,913,891 A | 4/1990 | Fowler | |
| 7,972,588 B2 * | 7/2011 | Arstad et al. | ................ 424/1.69 |
| 2002/0006947 A1 | 1/2002 | Hogenkamp et al. | |

FOREIGN PATENT DOCUMENTS

| | | |
|---|---|---|
| WO | 03/006491 | 1/2003 |
| WO | 03/101972 | 12/2003 |
| WO | 2004/055160 | 7/2004 |
| WO | 2004/094593 | 11/2004 |
| WO | 2005/003294 | 1/2005 |
| WO | 2006038184 | 4/2006 |

OTHER PUBLICATIONS

Deiters Alexander et al: "Adding amino acids with novel reactivity to the genetic code of *Saccharomyces cerevisiae*." Journal of the American Chemical Society Oct. 1, 2003, vol. 125, No. 39, Oct. 1, 2003, pp. 11782-11783, XP002469881 ISSN: 0002-7863.

Link A James et al: "Cell surface labeling of *Escherichia coli* via copper(I)-catalyzed [3+2] cycloaddition." Journal of the American Chemical Society Sep. 17, 2003, vol. 125, No. 37, Sep. 17, 2003, pp. 11164-11165, XP002469882 ISSN: 0002-7863.

Hashizume Kazunari et al: "Synthesis of Positron Labeled Photoactive Compounds: 18F Labeled Aryl Azides for Positron Labeling of Biochemical Molecules" Journal of Organic Chemistry, American Chemical Society, Easton.; US LNKD—DOI:10.1021/JO00126A015, vol. 60, No. 21, Oct. 1, 1995, pp. 6680-6681.

Vanbrocklin H F et al: "The synthesis of 7alpha-methyl-substituted estrogens labeled with fluorine-18: potential breast tumor imaging agents" Steroids, Elsevier Science Publishers, New York, NY, US LNKD—DOI:10.1016/0039-128X(94)90043-4, vol. 59, No. 1, Jan. 1, 1994, pp. 34-45.

Dolle Frederic et al: "Efficient synthesis and formulation of (R)-(−)-(11C)Deprenyl, a selective radioligand for the quantification of MAO-B activity using PET" Journal of Labelled Compounds and Radiopharmaceuticals, vol. 45, No. 10, Sep. 2002, pp. 803-811.

Lange Christopher W et al: "Photoconjugation of 3-azido-5-nitrobenzyl-(18F)fluoride to an oligonucleotide aptamer" Journal of Labelled Compounds and Radiopharmaceuticals, vol. 45, No. 3, Mar. 15, 2002, pp. 257-268.

Guillouet S: "Synthesis of 18F-labelled 4-ethynyl-2-fluorobenzaldehyde, first step of a TpOH inhibitor: 4-Ethynyl-2-(18F)fluoro-pEPA." Journal of Labelled Compounds and Radiopharmaceuticals, vol. 46, No. Supplement 1, Aug. 2003, p. S154, XP008128452 & 15th International Symposium on Radiopharmaceutical Chemistry; Sydney, Australia; Aug. 10-14, 2003.

Blye R P et al: "Development and use of a radioimmunoassay for D-(−)-norgestrel 17beta-cyclopentane-carboxylate" Steroids, Elsevier Science Publishers, New York, NY, US LNKD—DOI:10.1016/0039-128X(86)90039-5, vol. 48, No. 1-2, Jul. 1, 1986, pp. 27-45.

Poethko T et al: "Two-step methodology for high-yield routine radiohalogenation of peptides: 18F-labeled RGD and Octreotide Analogs" Journal of Nuclear Medicine, Society of Nuclear Medicine, Reston, VA, US, vol. 45, No. 5, May 1, 2004, pp. 892-902.

GB0428012.9 Search report dated Mar. 11, 2005.

PCT/GB2005/004729 Int'l Search Report & Written Opinion dated May 30, 2007.

Haubner, R. et.al., "Radiolabeled tracers for imaging of tumor angiogenesis and evaluation of anti-angiogenic therapies" Current Pharmaceutical Design, Bentham Sciene Publishers, Schiphol, NL, vol. 10, No. 13, May 2004 pp. 1439-1455.

Kolb, H.C. et.al., "The growing impact of click chemistry on drug discovery" Elsevier Science Ltd., GB vol. 8, No. 24, Dec. 2003, pp. 1128-1137.

Mizutani Biomacromolecules 2002, vol. 3, pp. 668-675.

Senchou CMLS Cell Mol. Life Sci, vol. 61, 2004 pp. 502-509.

* cited by examiner

*Primary Examiner* — D L Jones

(57) ABSTRACT

The invention relates to radiodiagnostic and radiotherapeutic agents, including biologically active vectors labelled with radionuclides. It further relates to methods of making such radiodiagnostic and radiotherapeutic agents and the compounds used in such methods. The resultant labelled conjugates are useful as diagnostic agents, for example, as radiopharmaceuticals more specifically for use in Positron Emission Tomography (PET) or Single Photon Emission Computed Tomography (SPECT) or for radiotherapy.

9 Claims, No Drawings

RADIOLABELLING METHODS

This application is a divisional of and claims benefit of priority under 35 U.S.C 120 of co-pending U.S. application Ser. No. 11/721,694 filed Jun. 14, 2007, which in turn is a filing under 35 U.S.C. 371 of international application number PCT/GB2005/004729, filed Dec. 9, 2005, which claims priority to application number 0428012.9 filed Dec. 22, 2004, in Great Britain the entire disclosure of each of which is hereby incorporated by reference.

The present invention relates to radiodiagnostic and radiotherapeutic agents, including biologically active vectors labelled with radionuclides. It further relates to methods and reagents labelling a vector such as a peptide. The resultant labelled conjugates are useful as diagnostic agents, for example, as radiopharmaceuticals more specifically for use in Positron Emission Tomography (PET) or Single Photon Emission Computed Tomography (SPECT) or for radiotherapy.

The application of radiolabelled bioactive peptides for diagnostic imaging is gaining importance in nuclear medicine. Biologically active molecules which selectively interact with specific cell types are useful for the delivery of radioactivity to target tissues. For example, radiolabelled peptides have significant potential for the delivery of radionuclides to tumours, infarcts, and infected tissues for diagnostic imaging and radiotherapy. $^{18}$F, with its half-life of approximately 110 minutes, is the positron-emitting nuclide of choice for many receptor imaging studies. Therefore, $^{18}$F-labelled bioactive peptides have great clinical potential because of their utility in PET to quantitatively detect and characterise a wide variety of diseases. Other useful radionuclides include $^{11}$C, radioiodine such as $^{125}$I, $^{123}$I, $^{124}$I, $^{131}$I and $^{99m}$Tc.

To date, a lack of rapid and generally applicable methods for peptide and biomolecule labelling has hampered the use of peptides and biomolecules as diagnostic agents. For example, almost all of the methodologies currently used today for the labelling of peptides and proteins with $^{18}$F utilize active esters of the fluorine labelled synthon. As peptides and proteins may contain a multitude of functional groups capable of reaction with active esters these current methods are not site-specific. For example a peptide containing three lysine residues has three amine functions all equally reactive towards the labelled synthon. Therefore, there still exists a need for labelling agents such as $^{18}$F-labelled prosthetic groups and methodologies, which allow rapid, chemoselective introduction of a label such as a radionuclide, for example $^{18}$F, particularly into peptides, under mild conditions to give labelled products in high radiochemical yield and purity. Additionally, there is a need for such methodologies which are amenable to automation to facilitate preparation of diagnostic agents in the clinical setting.

The present invention provides a method for labelling a vector comprising reaction of a compound of formula (I) with a compound of formula (II):

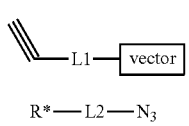

(I)

$$R^* - L2 - N_3$$

(II)

or, a compound of formula (III) with a compound of formula (IV)

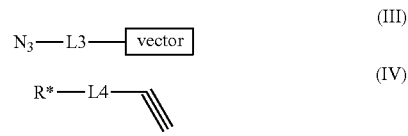

(III)

(IV)

in the presence of a Cu (I) catalyst, wherein:
L1, L2, L3, and L4 are each Linker groups;
R* is a reporter moiety which comprises a radionuclide;
to give a conjugate of formula (V) or (VI) respectively:

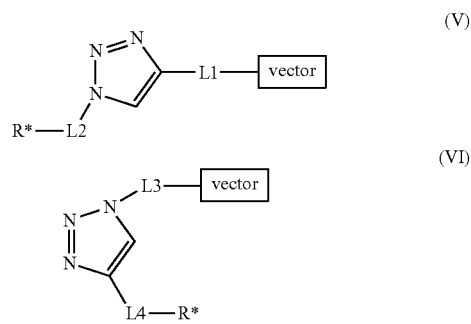

(V)

(VI)

wherein L1, L2, L3, L4, and R* are as defined above.

The Linker groups L1, L2, L3, and L4 are each independently a $C_{1-60}$ hydrocarbyl group, suitably a $C_{1-30}$ hydrocarbyl group, optionally including 1 to 30 heteroatoms, suitably 1 to 10 heteroatoms such as oxygen or nitrogen. Suitable Linker groups include alkyl, alkenyl, alkynyl chains, aromatic, polyaromatic, and heteroaromatic rings any of which may be optionally substituted for example with one or more ether, thiooether, sulphonamide, or amide functionality, monomers and polymers comprising ethyleneglycol, amino acid, or carbohydrate subunits.

The term "hydrocarbyl group" means an organic substituent consisting of carbon and hydrogen, such groups may include saturated, unsaturated, or aromatic portions.

The Linker groups L1, L2, L3, and L4 may be chosen to provide good in vivo pharmacokinetics, such as favourable excretion characteristics in the resultant compound of formula (V) or (VI). The use of linker groups with different lipophilicities and or charge can significantly change the in vivo pharmacokinetics of the peptide to suit the diagnostic need. For example, where it is desirable for a compound of formula (V) or (VI) to be cleared from the body by renal excretion, a hydrophilic linker is used, and where it is desirable for clearance to be by hepatobiliary excretion a hydrophobic linker is used. Linkers including a polyethylene glycol moiety have been found to slow blood clearance which is desirable in some circumstances.

R* is a reporter moiety which comprises a radionuclide for example a positron-emitting radionuclide. Suitable positron-emitting radionuclides for this purpose include $^{11}$C, $^{18}$F, $^{75}$Br, $^{76}$Br, $^{124}$I, $^{82}$Rb, $^{68}$Ga, $^{64}$Cu and $^{62}$Cu, of which $^{11}$C and $^{18}$F are preferred. Other useful radionuclides include $^{123}$I, $^{125}$I, $^{131}$I, $^{211}$At, $^{99m}$Tc, and $^{111}$In. Metallic radionuclides are suitably incorporated into a chelating agent, for example by direct incorporation by methods known to the person skilled in the art. Chelation of a metallic reporter is preferably performed prior to reaction of the compound of formula (I) or (IV) with a compound of formula (II) or (III) respectively, to avoid chelation of the Cu(I) catalyst.

Suitable chelating agents comprised in R*, include those of Formula X

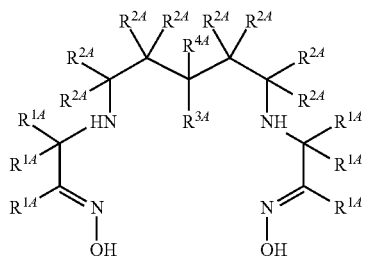

where:

each $R^{1A}$, $R^{2A}$, $R^{3A}$ and $R^{4A}$ is independently an $R^A$ group;

each $R^A$ group is independently H or $C_{1-10}$ alkyl, $C_{3-10}$ alkylaryl, $C_{2-10}$ alkoxyalkyl, $C_{1-10}$ hydroxyalkyl, $C_{1-10}$ alkylamine, $C_{1-10}$ fluoroalkyl, or 2 or more $R^A$ groups, together with the atoms to which they are attached form a carbocyclic, heterocyclic, saturated or unsaturated ring, or R* can comprise a chelating agent given by formula (i), (ii), (iii), or (iv)

(i)

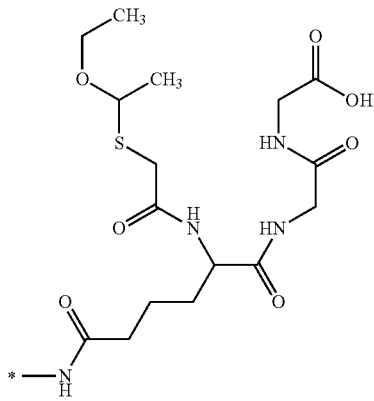

(ii)

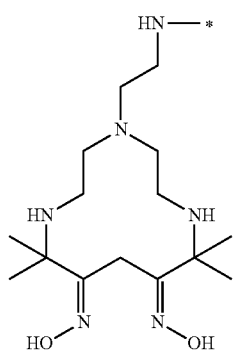

(iii)

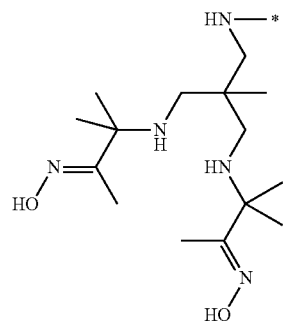

(iv)

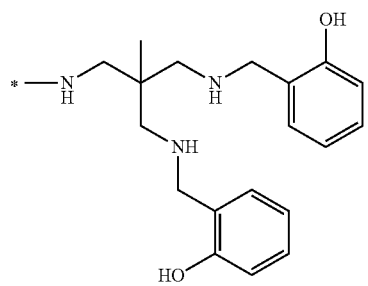

A preferred example of a chelating agent is represented by formula (v).

(v)

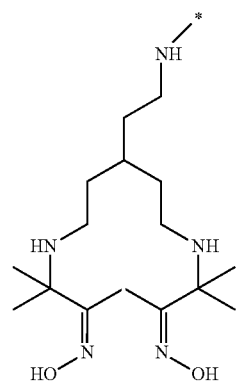

Compounds of formula (II) or (IV) comprising chelating agents of Formula X can be radiolabelled to give good radiochemical purity (RCP), at room temperature, under aqueous conditions at near neutral pH.

In formulae (I) and (III) and in other aspects of the invention unless specifically stated otherwise, suitable vectors for labelling are peptides, which may include somatostatin analogues, such as octreotide, bombesin, vasoactive intestinal peptide, chemotactic peptide analogues, α-melanocyte stimulating hormone, neurotensin, Arg-Gly-Asp peptide, human pro-insulin connecting peptide, insulin, endothelin, angiotensin, bradykinin, endostatin, angiostatin, glutathione, calcitonin, Magainin I and II, luteinizing hormone releasing hormone, gastrins, cholecystochinin, substance P, vasopressin, formyl-norleucyl-leucyl-phenylalanyl-norleucyl-tyrosyl-lysine, Annexin V analogues, Vasoactive Protein-1 (VAP-1) peptides, and caspase peptide substrates. Preferred peptides for labelling are Arg-Gly-Asp peptide and its analogues, such as those described in WO 01/77415 and WO 03/006491, preferably a peptide comprising the fragment

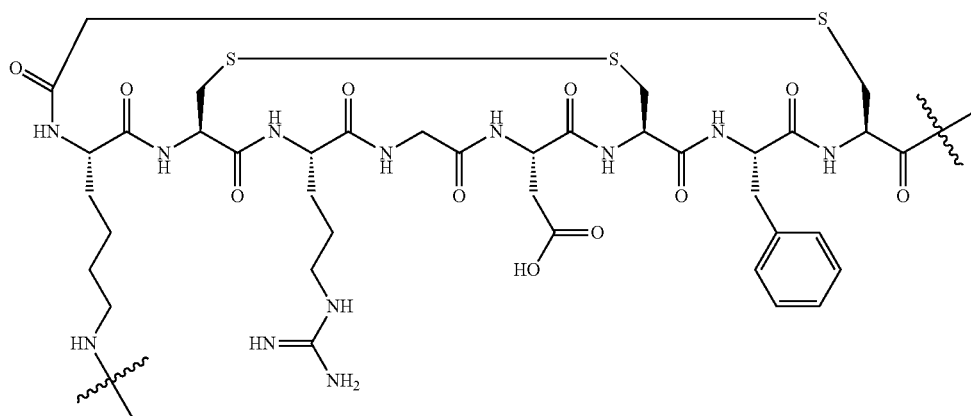

more preferably the peptide of formula (A):

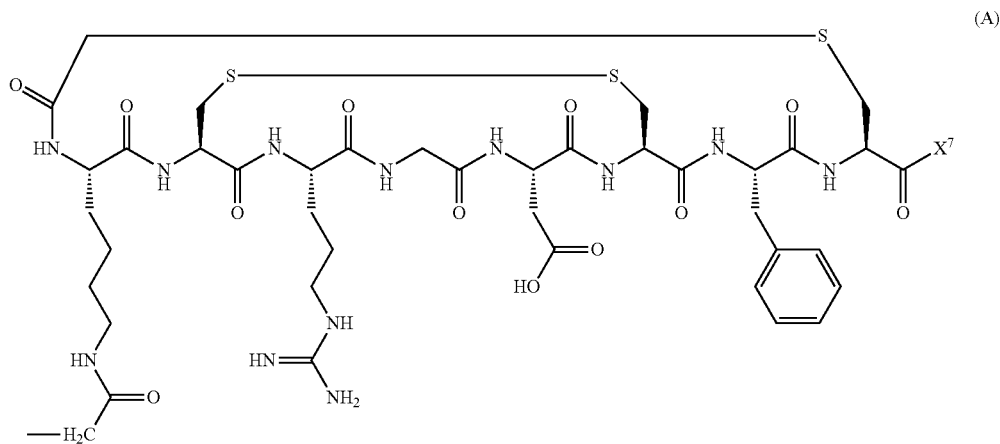

wherein $X^7$ is either —$NH_2$ or

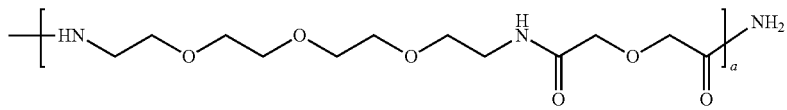

wherein a is an integer of from 1 to 10, preferably a is 1.

As will be appreciated by the skilled person, the methods of the invention may also be used for radiolabelling of other biomolecules such as proteins, hormones, polysaccharides, oligonucleotides, and antibody fragments, cells, bacteria, viruses, as well as small drug-like molecules to provide a variety of diagnostic agents. In formulae (I) and (III) and in other aspects of the invention unless specifically stated otherwise, particularly suitable vectors for radiolabelling are peptides, proteins, hormones, cells, bacteria, viruses, and small drug-like molecules.

The reaction of compound of formula (I) with compound of formula (II) or of compound of formula (III) with compound of formula (IV) may be effected in a suitable solvent, for example acetonitrile, a $C_{1-4}$ alkylalcohol, dimethylformamide, tetrahydrofuran, or dimethylsulphoxide, or aqueous mixtures of any thereof, or in water and at a non-extreme temperature of from 5 to 100° C., preferably at ambient temperature. The Cu(I) catalyst is present in an amount sufficient for the reaction to progress, typically either in a catalytic amount or in excess, such as 0.02 to to 1.5 molar equivalents relative to the compound of formula (I) or (III).

Suitable Cu(I) catalysts include Cu(I) salts such as CuI, CuOTf.$C_6H_6$ or [Cu(NCCH$_3$)$_4$][PF$_6$], but advantageously Cu(II) salts such as copper (II) sulphate may be used in the presence of a reducing agent such as ascorbic acid or a salt thereof for example sodium ascorbate, hydroquinone, quinone, metallic copper, glutathione, cysteine, $Fe^{2+}$, or $Co^{2+}$. Cu(I) is also intrinsically presented on the surface of elemental copper particles, thus elemental copper, for example in the form of powder or granules may also be used as catalyst. It has been found that using a Cu(I) catalyst, particularly elemental copper, with controlled particle size, leads to surprisingly improved radiochemical yields. Thus, in one aspect of the invention, the Cu (I) catalyst particularly elemental copper, has a particle size in the range of from 0.001 to 1 mm, preferably of from 0.1 mm to 0.7 mm, more preferably around 0.4 mm.

The present invention provides a more chemoselective approach to radiolabelling where the exact site of introduction of the label is pre-selected during the synthesis of the peptide or vector precursor. The ligation reaction occurring at a pre-determined site in the vector gives only one possible product. This methodology is therefore chemoselective, and its application is considered generic for a wide range of peptides, biomolecules and low-molecular weight drugs. Additionally, both alkyne and azide functionalities are stable under most reaction conditions and are unreactive with most common peptide functionalities—thus minimising the protection and deprotection steps required during the labelling synthesis. Furthermore, the triazole ring formed during the labelling reaction does not hydrolise and is highly stable to oxidation and reduction, meaning that the labelled vector has high in vivo stability. The triazole ring is also comparible to an amide in size and polarity such that the labelled peptides or proteins are good mimics for their natural counterparts.

Compounds of formula (I) and (III) wherein the vector is a peptide or protein may be prepared by standard methods of peptide synthesis, for example, solid-phase peptide synthesis, for example, as described in Atherton, E. and Sheppard, R. C.; "Solid Phase Synthesis"; IRL Press: Oxford, 1989. Incorporation of the alkyne or azide group in a compound of formula (I) or (III) may be achieved by reaction of the N or C-terminus of the peptide or with some other functional group contained within the peptide sequence, modification of which does not affect the binding characteristics of the vector. The alkyne or azide groups are preferably introduced to a compound of formula (I) or (III) by formation of a stable amide bond, for example formed by reaction of a peptide amine function with an activated acid or alternatively reaction of a peptide acid function with an amine function and introduced either during or following the peptide synthesis. Methods for incorporation of the alkyne or azide group into vectors such as cells, viruses, bacteria may be found in H. C. Kolb and K. B. Sharpless, Drug Discovery Today, Vol 8 (24), December 2003 and the references therein. Suitable intermediates useful for incorporation of the alkyne or azide group in a compound of formula (I) or (III) include:

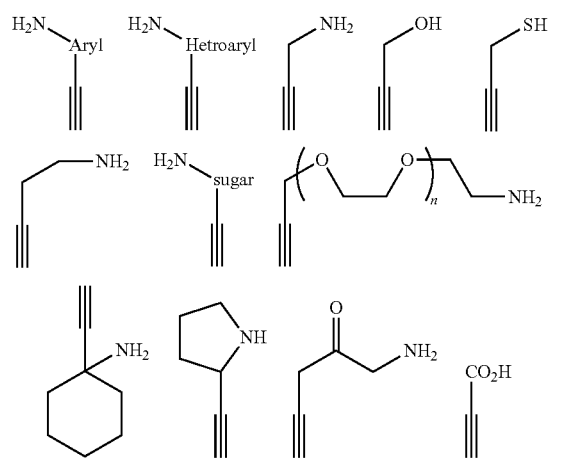

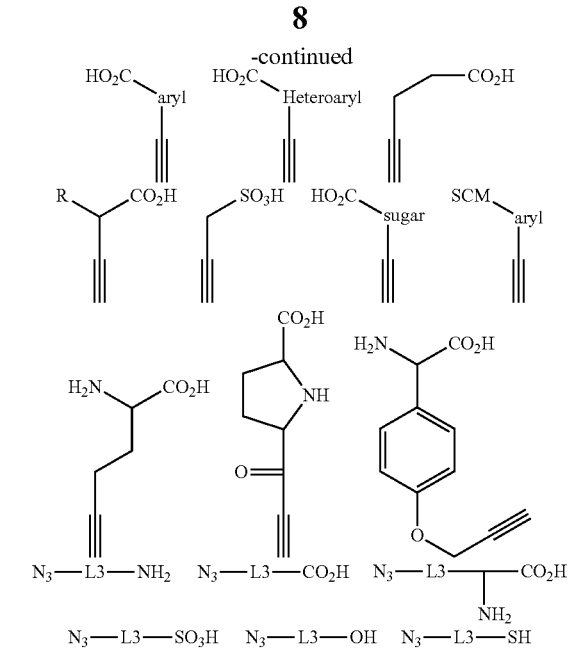

In another aspect, the present invention provides novel prosthetic groups, useful for labelling vectors such as peptides and proteins, for example by the methods described above. Accordingly, there is provided a compound of formula (II) or formula (IV):

wherein L2 and L4 are each Linker groups as defined above and R* is a reporter moiety as defined above. In one embodiment of this aspect of the invention, R* is $^{18}F$ such that the prosthetic groups are of formula (IIa) and (IVa):

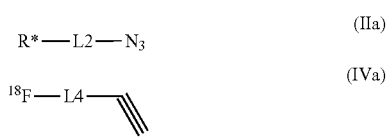

wherein L2 and L4 are each Linker groups as defined above.
Preferred compounds of formula (IV) include:

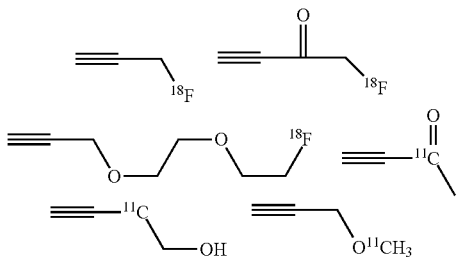

In another aspect, the present invention provides a compound of formula (I) or (III):

-continued

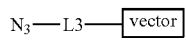
(III)

wherein L1 and L3 are each Linker groups as defined above and the vector is as defined above. Suitably, in this aspect of the invention the vector is a peptide or protein. Preferred compounds of formula (I) and (III) are those wherein the vector is Arg-Gly-Asp peptide or an analogue thereof such as those described in WO 01/77415 and WO 03/006491, preferably a peptide comprising the fragment

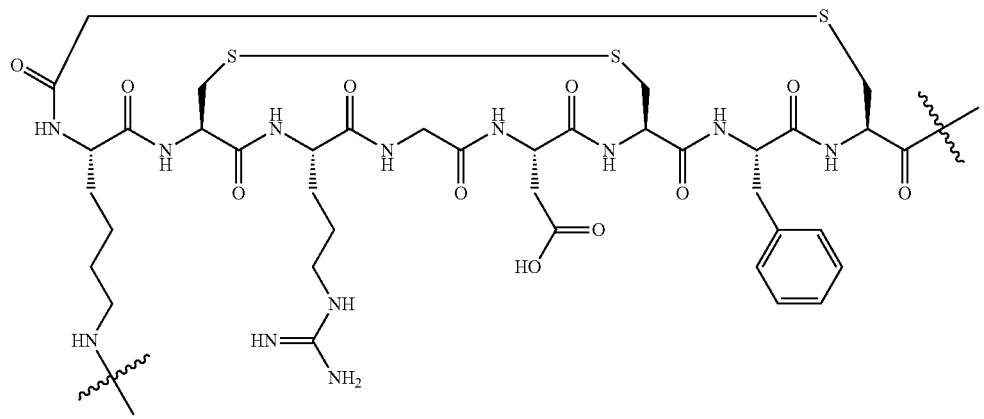 [SMILES: *NCCCC[C@@H]1NC(=O)CSC[C@@H](C(*)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]

more preferably the peptide of formula (A):

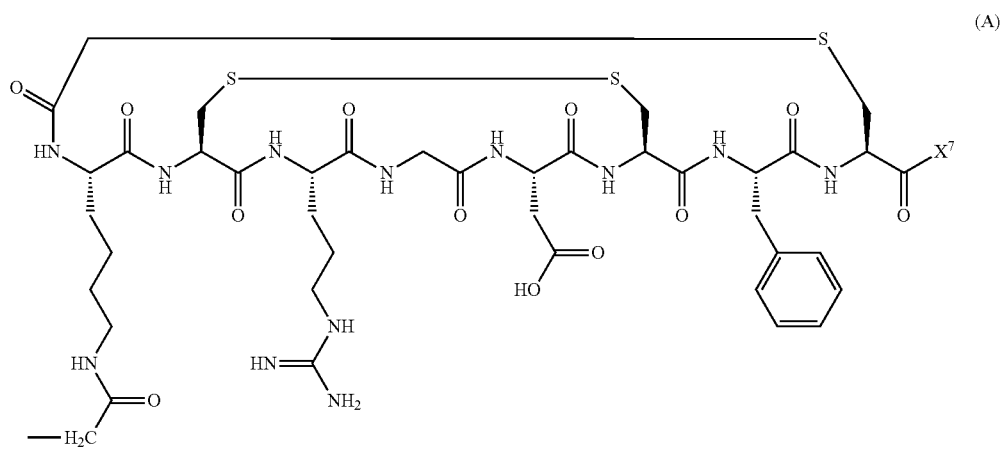
(A)

wherein $X^7$ is either —NH$_2$ or

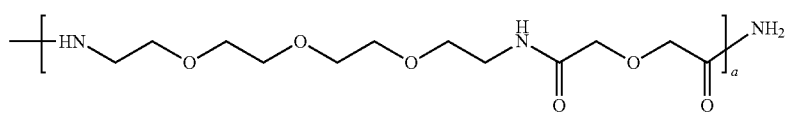

wherein a is an integer of from 1 to 10, preferably a is 1.

In a further aspect the present invention provides labelled vectors of formulae (V) and (VI), as defined above. Preferred compounds of formulae (V) and (VI), are those wherein the vector is Arg-Gly-Asp peptide or an analogue thereof, such as those described in WO 01/77415 and WO 03/006491, preferably a peptide comprising the fragment

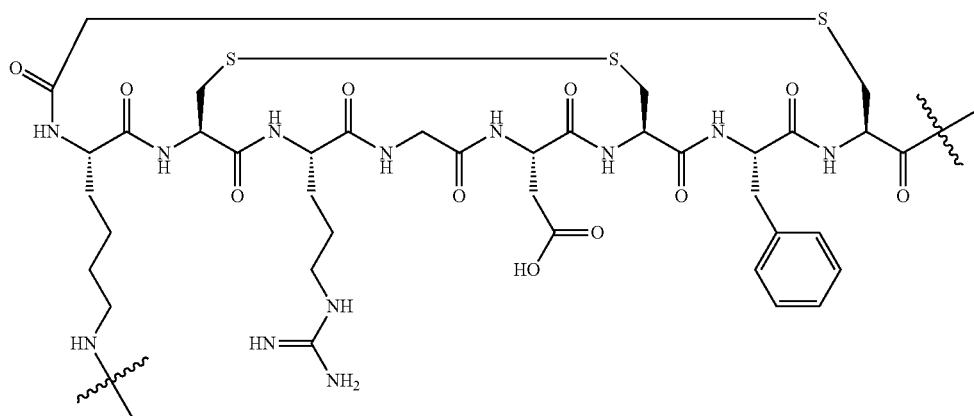

more preferably the peptide of formula (A):

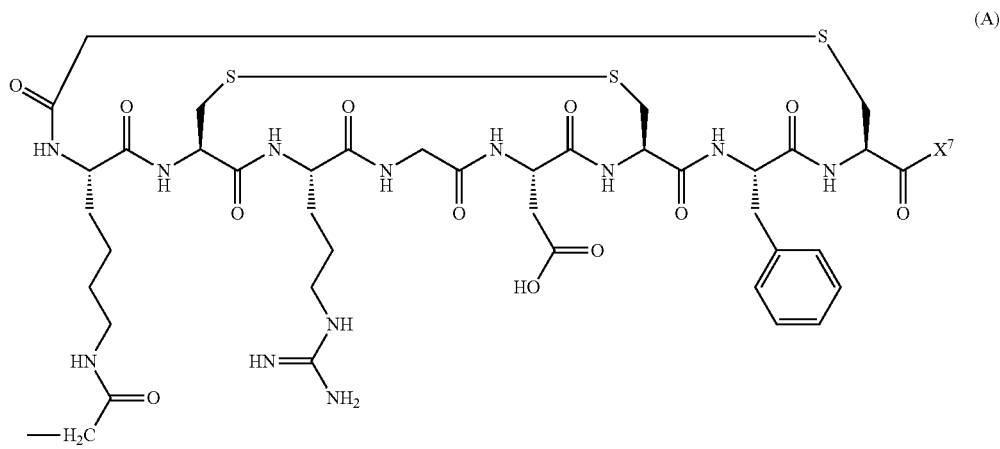

wherein $X^7$ is either —$NH_2$ or

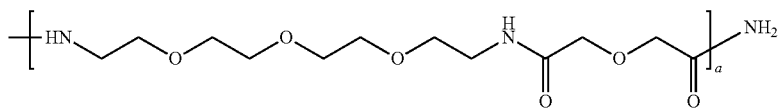

wherein a is an integer of from 1 to 10, preferably a is 1.

Compounds of formula (II) wherein R* comprises a $^{11}C$ radiolabel may be prepared for example according to the scheme:

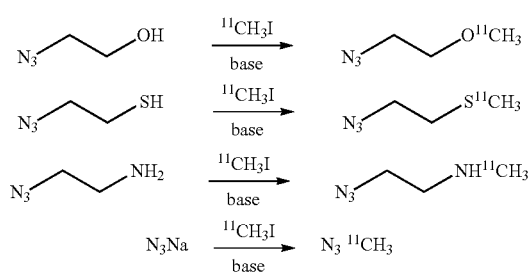

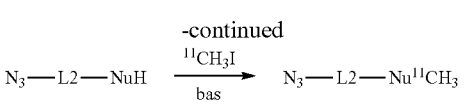

wherein -NuH is a nucleophilic reactive centre such as a hydroxyl, thiol or amine functionality.

Compounds of formula (II) wherein R* is $^{18}F$, may be prepared by either electrophilic or nucleophilic fluorination reactions, for example:

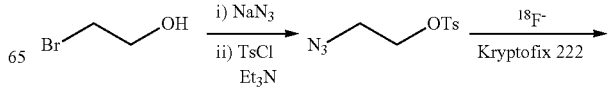

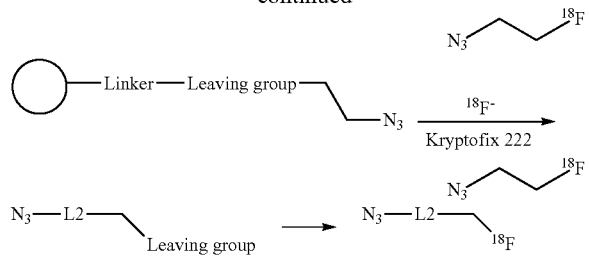

Suitable radiofluorination methods for preparation of a compound of formula (II) include reaction of the precursor incorporating a leaving group (such as an alkyl or aryl sulphonate, for example mesylate, triflate, or tosylate; nitro, or a trialkylammonium salt) with 18F⁻ in the presence of a phase transfer agent such as a cyclic polyether, for example 18-Crown-6 or Kryptofix 2.2.2. This reaction may be performed in solution phase (using an aprotic solvent such as acetonitrile as solvent) under standard conditions known in the art [for example, M. J. Welch and C. S. Redvanly "Handbook of Radiopharmaceuticals", published by Wiley], or using a solid support to facilitate purification of the compound of formula (II) using the methods described in WO 03/002157.

Compounds of formula (IV) may be prepared from suitable acetylene precursors by methods analogous to those described for synthesis of compounds of formula (II).

The present invention also provides a radiopharmaceutical composition comprising an effective amount (e.g. an amount effective for use in in vivo imaging, suitably PET or SPECT) of a compound of general formula (V) or (VI) as defined above; together with one or more pharmaceutically acceptable adjuvants, excipients or diluents. Preferably, the vector in the compound of formula (V) or (VI) is Arg-Gly-Asp peptide or an analogue thereof, as described above.

A further embodiment of the invention relates to a compound of general formula (V) or (VI) as defined above, for medical use and particularly for use in in vivo imaging (suitably by PET or SPECT). Preferably, the vector in the compound of formula (V) or (VI) is Arg-Gly-Asp peptide or an analogue thereof, as described above.

The labelled vectors of formulae (V) and (VI) may be administered to patients for in vivo imaging in amounts sufficient to yield the desired signal, typical radionuclide dosages for PET or SPECT imaging of 0.01 to 100 mCi, preferably 0.1 to 50 mCi will normally be sufficient per 70 kg bodyweight.

The labelled vectors of formula (V) or (VI) may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

Viewed from a further aspect the invention provides the use of a labelled vector of formula (V) or (VI) for the manufacture of a pharmaceutical for use in a method of in vivo imaging, suitably PET; involving administration of said pharmaceutical to a human or animal body and generation of an image of at least part of said body.

Viewed from a still further aspect the invention provides a method of generating an image of a human or animal body involving administering a pharmaceutical to said body, e.g. into the vascular system and generating an image of at least a part of said body to which said pharmaceutical has distributed using an in vivo imaging technique such as PET, wherein said pharmaceutical comprises a labelled vector of formula (V) or (VI).

Viewed from a further aspect the invention provides a method of monitoring the effect of treatment of a human or animal body with a drug to combat a condition, said method comprising administering to said body a labelled vector of formula (V) or (VI) and detecting the uptake of said labelled vector, said administration and detection optionally but preferably being effected repeatedly, e.g. before, during and after treatment with said drug.

In yet another embodiment of the instant invention, there is provided a kit for the preparation of a radiofluorinated tracer comprising a prosthetic group of formula (II) or (IV) or a precursor thereof and a compound of formula (I) or (III).

In use of the kits, the precursor compound would be converted to the corresponding compound of formula (II) or (IV), using methods described above. The compounds of formula (II) and (IV) may be used in unpurified form, but preferably, the compound of formula (II) and (IV) may be separated from waste reactants by passing the reaction mixture through a Solid Phase Extraction (SPE) cartridge, by chromatography, or by distillation. The compound of formula (II) and (IV) would then be added to the compounds of formula (I) and (III) respectively which may suitably be dissolved in a suitable solvent as described herein. After reaction at a non-extreme temperature for 1 to 90 minutes, the labelled peptide may be purified, for example, by SPE and collected.

The chemistry described herein may also be used to prepare libraries of radiolabelled vectors suitable for screening as diagnostic drugs or in vivo imaging agents. Thus, a mixture of prosthetic groups of formula (II) or (IV) may be reacted with one or more compounds of formula (I) or (III) respectively using the methods described above to yield a library of radiolabelled vectors.

EXAMPLES

The invention is illustrated by way of examples in which the following abbreviations are used:
HPLC: high performance liquid chromatography
DMF: N,N-dimethylformamide
DMSO: dimethylsulphoxide
ESI-MS: Electrospray Ionisation Mass Spectrometry
r.t.: room temperature
TOF-ESI-MS: time of flight electrospray ionisation mass spectrometry
FT-IR: Fourier transform infrared
ppm: parts per million
TFA: trifluoroacetic acid
ACN: acetonitrile Preparation of Reference Compounds

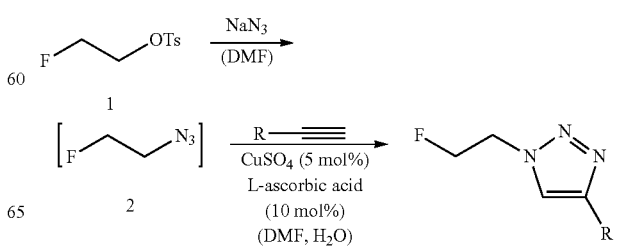

-continued

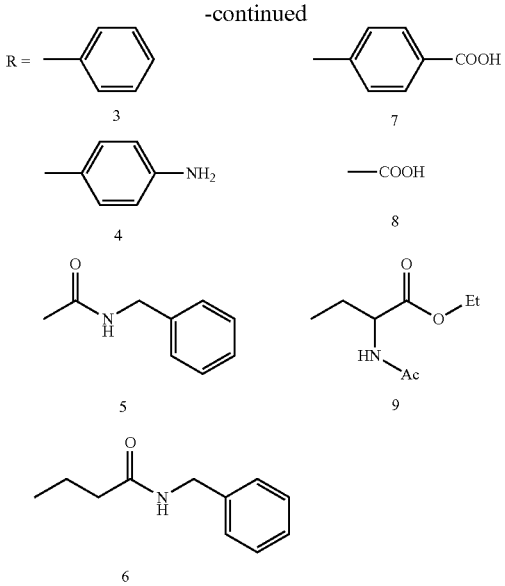

Example 1

Preparation of Compound (2)

1-Azido 2-fluoroethane

Toluene-4-sulfonic acid 2-fluoro-ethyl ester, compound (1), was prepared as described by E. U. T. van Velzen et al. in Synthesis (1995) 989-997. Compound (1) (128 mg, 0.586 mmol) and sodium azide (114 mg, 1.758 mmol) were mixed with anhydrous DMF (10 ml) and stirred at room temperature for 48 hours. The reaction mixture was filtered, but product (2) was not isolated from the reaction solution.

Example 2

Preparation of Compound (3)

1-(2-Fluoro-ethyl)-4-phenyl-1H-[1,2,3]triazole

Phenylacetylene (105 µl, 0.977 mmol) in DMF (1 ml) was added under nitrogen to a stirring solution of copper(II) sulphate pentahydrate (12 mg, 0.0489 mmol) and L-ascorbic acid (16 mg, 0.0977 mmol) in water (0.3 ml). After addition of compound (2) (1.172 mmol) in DMF (5 ml), stirring was continued at room temperature for 21 hours. The reaction mixture was diluted with water (5 ml), and the crude product was extracted with dichloromethane (3×5 ml) and washed with sodium bicarbonate solution (10%, 3×10 ml), and brine (1×5 ml). After drying over sodium sulphate, the solvent is removed under reduced pressure and the crude material purified using flash chromatography (silica, hexane/ethylacetate).

Yield: 32 mg (17%) white crystals, m.p. 83-85° C.
$^1$H-NMR (CDCl$_3$): δ=4.70 (m, 1H, CH$_2$), 4.76 (m, 1H, CH$_2$), 4.80 (m, 1H, CH$_2$), 4.89 (m, 1H, CH$_2$), 7.35 (tt, 1.0 Hz, 7.5 Hz, 1H, HAr), 7.44 (m, 2H, HAr), 7.84 (m, 2H, HAr), 7.89 (d, 1 Hz, 1H, CH-triazole) ppm
GC-MS: m/z=191
TOF-ESI-MS: found m/z=192.0935 [MH]$^+$, calculated for C$_{10}$H$_{10}$N$_3$F [MH]$^+$ m/z=192.0932

Example 3

Preparation of Compound (4)

4-[1-(2-Fluoro-ethyl)-1H-[1,2,3]triazol-4-yl]-phenylamine

4-Ethynylaniline (40 mg, 0.344 mmol) in DMF (0.7 ml) was added under nitrogen to a stirring solution of copper(II) sulphate pentahydrate (129 mg, 0.516 mmol) and L-ascorbic acid (182 mg, 1.032 mmol) in water (1.2 ml). After addition of compound (2) (0.287 mmol) in DMF (2.45 ml), stirring was continued at room temperature for 4 hours. The reaction mixture was quenched with sodium hydroxide solution (1M, 5 ml). The product was extracted with ethyl acetate (3×5 ml), washed with water (5 ml), and brine (2 ml). After drying over sodium sulphate, the solvent was removed under reduced pressure and the crude material purified using flash chromatography (silica, hexane/ethylacetate). Yield: 15 mg (25%) beige crystals, m.p. 79-82° C.
$^1$H-NMR (CDCl$_3$): δ=4.70 (m, 1H, CH$_2$), 4.72 (m, 1H, CH$_2$), 4.77 (m, 1H, CH$_2$), 4.88 (m, 1H, CH$_2$), 6.74 (m, 2H, HAr), 7.63 (m, 2H, HAr), 7.74 (d, 0.1 Hz, 1H, CH-triazole) ppm
TOF-ESI-MS: found m/z=207.1030 [MH]$^+$, calculated for C$_{10}$H$_{11}$N$_4$F [MH]$^+$ m/z=207.1040

Example 4

Preparation of Compound (5)

1-(2-Fluoro-ethyl)-1H-[1,2,3]triazole-4-carboxylic acid benzylamide

Propynoic acid benzylamide (50 mg, 0.314 mmol) that was prepared following the protocol of G. M. Coppola and R. E. Damon in Synthetic Communications 23 (1993) 2003-2010, was dissolved in DMF (1 ml) and added under nitrogen to a stirring solution of copper(II) sulphate pentahydrate (3.9 mg, 0.0157 mmol) and L-ascorbic acid (11 mg, 0.0628 mmol) in water (0.4 ml). After addition of compound (2) (0.377 mmol) in DMF (3.2 ml), stirring was continued at room temperature for 48 hours. The reaction mixture was diluted with sodium bicarbonate (10%, 5 ml), and the crude product was extracted with dichloromethane (3×5 ml) and washed with brine (5 ml). After drying over sodium sulphate, the solvent was removed under reduced pressure and the crude material purified by recrystallization from ethylacetate/diethylether.

Yield: 8 mg (10%) white crystals, m.p. 165-167° C.
$^1$H-NMR (CDCl$_3$): δ=4.70 (m, 6H, CH$_2$), 7.34 (m, 5H, HAr), 7.46 (m, 1H, NH), 8.20 (s, 1H, CH-triazole) ppm
TOF-ESI-MS: found m/z=249.1143 [MH]$^+$, calc. for C$_{12}$H$_{13}$N$_4$OF [MH]$^+$ m/z=249.1146

Example 5

Preparation of Compound (6)

N-Benzyl-3-[1-(2-fluoro-ethyl)-1H-[1,2,3]triazol-4-yl]-propionamide

Pent-4-ynoic acid benzylamide

This compound was synthesised using a similar method as described by G. M. Coppola and R. E. Damon (see example 4) except with isolating of the N-succinimidyl intermediate.

Yield: 100 mg (53%) white needles, m.p. 50-55° C.
$^1$H-NMR (CDCl$_3$): δ=1.98 (m, 1H, alkyne-CH), 2.44 (m, 2H, CH$_2$), 2.56 (m, 2H, CH$_2$), 4.46 (d, 2H, CH$_2$N), 7.29-7.25 (m, 5H, HAr) ppm
FT-IR (film): 1651, 1629 cm$^{-1}$
TOF-ESI-MS: found m/z=188.1073 [MH]$^+$, calc. for C$_{12}$H$_{13}$NO [MH]$^+$ m/z=188.1070

N-Benzyl-3-[1-(2-fluoro-ethyl)-1H-[1,2,3]triazol-4-yl]-propionamide

Pent-4-ynoic acid benzylamide (50 mg, 0.267 mmol) in methanol (0.5 ml), compound (2) (0.320 mmol) in DMF (2.62 ml), and diisopropylamine (0.233 ml, 1.335 mmol) are added under nitrogen to a stirring suspension of copper(I) iodide (255 mg, 1.335 mmol) in methanol (0.8 ml). Stirring was continued at room temperature for 2 hours. The reaction mixture was quenched with a solution of sodium hydrogenphosphate (1 g) in water (10 ml) and filtered through Celite. The crude product was extracted with ethyl acetate (3×20 ml), and washed with brine (20 ml). After drying over sodium sulphate, the solvent was removed under reduced pressure and the crude material purified by column chromatography using silica and ethylacetate/hexane.
Yield: 19 mg (26%) white crystals, m.p. 127-133° C.
$^1$H-NMR (CDCl$_3$): δ=2.66 (t, 7.0 Hz, 2H, CH$_2$), 3.09 (t, 7.0 Hz, 2H, CH$_2$), 4.40 (d, 5.7 Hz, 2H, benzyl-CH$_2$), 4.56 (m, 2H, CH$_2$), 4.61 (m, 2H, CH$_2$), 4.70 (m, 2H, CH$_2$), 4.80 (m, 2H, CH$_2$), 6.0 (s, 1H, NH), 7.0-7.3 (m, 5H, HAr), 7.44 (s, 1H, CH-triazole) ppm
TOF-ESI-MS: found m/z=277.1474 [MH]$^+$, calc. for C$_{12}$H$_{13}$N$_4$OF [MH]$^+$ m/z=277.1459

Example 6

Preparation of Compound (7)

4-[1-(2-Fluoro-ethyl)-1H-[1,2,3]triazol-4-yl]-benzoic acid

Sodium 4-ethynylbenzoate (50 mg, 0.297 mmol) in DMF (1.5 ml) was added under nitrogen to a stirring solution of copper(II) sulphate pentahydrate (3.7 mg, 0.0149 mmol) and L-ascorbic acid (10.5 mg, 0.0595 mmol) in water (0.2 ml). After addition of compound (2) (0.356 mmol) in DMF (0.76 ml), stirring was continued at room temperature for 12 hours. The reaction mixture was diluted with HCl (20 ml, 1M). The crude product was extracted with ethyl acetate (3×10 ml) and washed with brine (10 ml). After drying over sodium sulphate, the solvent was removed under reduced pressure and the crude material recrystalized from ethylacetate/hexane.
Yield: 37 mg (52%) white crystals, m.p. 236-240° C.
$^1$H-NMR (DMSO-d$_6$): δ=4.74 (m, 1H, CH$_2$), 4.80 (m, 2H, CH$_2$), 4.90 (m, 1H, CH$_2$), 8.70 (s, 1 Hz, 1H, CH-triazole) ppm
TOF-ESI-MS: found m/z=236.0838 [MH]$^+$, calc. for C$_{11}$H$_{10}$N$_3$O$_2$F [MH]$^+$ m/z=236.0830

Example 7

Preparation of Compound (8)

1-(2-Fluoro-ethyl)-1H-[1,2,3]triazole-4-carboxylic acid

Propiolic acid (60 μl, 0.977 mmol) in DMF (0.5 ml) was added under nitrogen to a stirring solution of copper(II) sulphate pentahydrate (12 mg, 0.0489 mmol) and L-ascorbic acid (34 mg, 0.135 mmol) in water (0.4 ml). After addition of compound (2) (1.172 mmol) in DMF (2.5 ml), stirring was continued at room temperature for four hours. The reaction mixture was quenched with HCl (20 ml, 1M), and the crude product was extracted with ethyl acetate (3×20 ml). After washing with brine (5 ml) and drying over sodium sulphate, the solvent was removed under reduced pressure and the product purified by recrystallisation from ethyl acetate/hexane.
Yield: 16 mg (10%) white crystals, m.p. 160-165° C.
$^1$H-NMR (DMSO-d$_6$): δ=4.74 (m, 1H, CH$_2$), 4.80 (m, 2H, CH$_2$), 4.90 (m, 1H, CH$_2$), 8.71 (s, 1H, CH-triazole) ppm
TOF-ESI-MS: found m/z=160.0518 [MH]$^+$, calc. for C$_5$H$_6$N$_3$O$_2$F [MH]$^+$ m/z=160.0517

Example 8

Preparation of compound (9)

2-Acetylamino-3-[1-(2-fluoro-ethyl)-1H-[1,2,3]triazol-4-yl]-propionic acid ethyl ester 2-Acetylamino-pent-4-ynoic acid ethyl ester (200 mg, 1.09 mmol) in methanol (1 ml) was added under nitrogen to copper powder (200 mg, 40 mesh), followed by a solution of compound (2) (1.09 mmol) in DMF (3 ml). The mixture was stirred for 90 minutes and then heated at 80° C. for three hours. Compound (9) was isolated by reverse phase flash chromatography (acetonitrile/water).
Yield: 145 mg (49%) oil, crystals upon storing at 4° C., m.p. 55-60° C.
$^1$H-NMR (CDCl$_3$): δ=1.13 (t, 3H, CH$_2$CH$_3$), 1.82 (s, 3H, CH$_3$), 2.97 (dd, $^2$J=14.9 Hz, $^3$J=8.5 Hz, 1H, propionic-CH$_2$), 3.07 (dd, $^2$J=14.9 Hz, $^3$J=6.0 Hz, 1H, propionic-CH$_2$), 4.05 (m, 2H, OCH$_2$CH$_3$), 4.47 (m, 1H, CH), 4.46 (m, 1H, CH$_2$), 4.64 (m, 1H, CH$_2$), 4.70 (m, 1H, CH$_2$), 4.81 (m, 1H, CH$_2$), 7.89 (s, 1H, triazole-CH), 8.31 (d, 1H, NH) ppm
TOF-ESI-MS: found m/z=273.1372 [MH]$^+$, calc. for C$_{11}$H$_{17}$N$_4$O$_3$F [MH]$^+$ m/z=273.1357
Radiochemistry

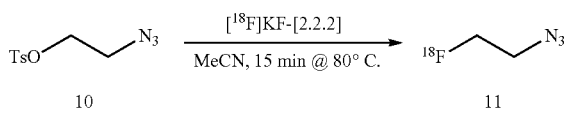

Example 9

Preparation of Compound (11)

[$^{18}$F]1-Azido-2-fluoro-ethane $^{18}$F-Fluoride was produced by a cyclotron using the $^{18}$O(p, n)$^{18}$F nuclear reaction with 19 MeV proton irradiation of an enriched [$^{18}$O]H$_2$O target. After the irradiation, a mixture of Kryptofix® (5 mg), potassium carbonate (1 mg), and acetonitrile (1 ml) was added to $^{18}$F-water (1 ml). The solvent was removed by heating at 80° C. under a stream of nitrogen (100 ml/min). Afterwards, acetonitrile (0.5 ml) was added and evaporated under heating and nitrogen stream. This procedure was repeated twice. After cooling to room temperature, a solution of compound (10) [1.5 μl; prepared according to the method of Z. P. Demko and K. B. Sharpless, Org. Lett. 3 (2001) 4091] in anhydrous acetonitrile (0.2 ml) was added. The reaction mixture was stirred for 30 min at 80° C. Compound (11) was isolated with a decay-corrected radiochemical yield of 40±14% (n=7) through distillation [efficiency: 76±8% (n=7)].

Example 10

Preparation of Compounds (12)-(16)

[¹⁸F][1-(2-Fluoro-ethyl)-1H-[1,2,3]triazoles

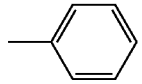

| Compound | R | R.C.Y.* |
|---|---|---|
| 12 | 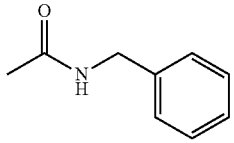 | 39%** |
| 13 | 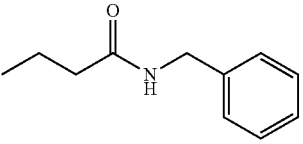 | 7% |
| 14 | 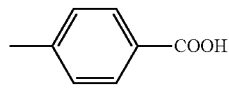 | <1% |
| 15 | 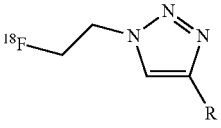 —COOH | 69% |

-continued

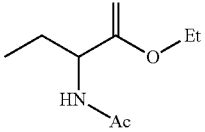

| Compound | R | R.C.Y.* |
|---|---|---|
| 16 | 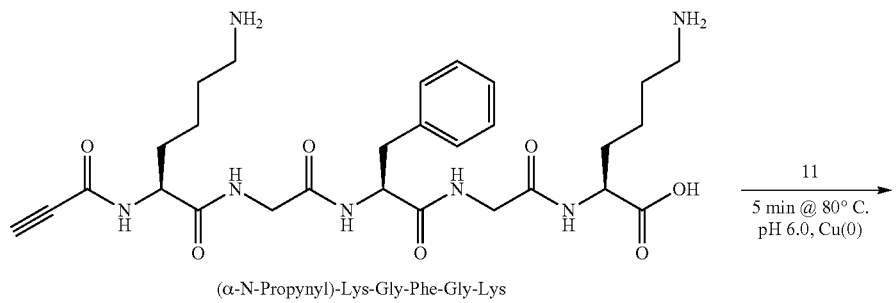 | >99% |

*by HPLC,
**isolated, one-pot reaction

A solution of the alkyne reagent (0.015 mmol) in DMF (0.1 ml) was added to a mixture of copper(II) sulphate (5 equivalents) and L-ascorbic acid (20 equivalents) under nitrogen. A solution of compound (11) in acetonitrile (0.2 ml) was added. After stirring for 30 min at 80° C., the reaction mixture was analyzed by HPLC.

Example 11

Preparation of Compound (18)

[¹⁸F](S)-6-Amino-2-(2-{(S)-2-[2-((S)-6-amino-2-{[4-(2-fluoro-ethyl)-[1,2,3]triazole-1-carbonyl]-amino}-hexanoylamino)-acetylamino]-3-phenyl-propionylamino}-acetylamino)-hexanoic acid

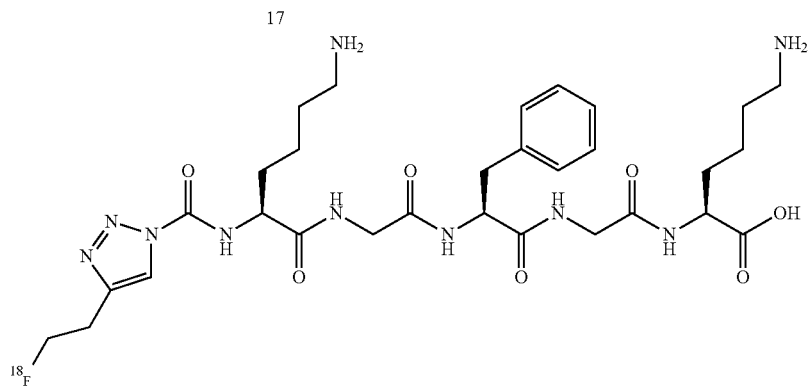

Compound (17) (1 mg, 1.7 μmol) was dissolved in sodium phosphate buffer (pH 6.0, 0.25 M, 0.05 ml). Compound (11) (175 μCi, 6.5 MBq) in acetonitrile (0.05 ml) was added followed by copper granules (400 mg, 10-40 mesh). The mixture was heated for 5 minutes at 80° C. HPLC analysis shows 86% of radiolabelled peptide (18).
Example 12
Preparation of Compound (20)
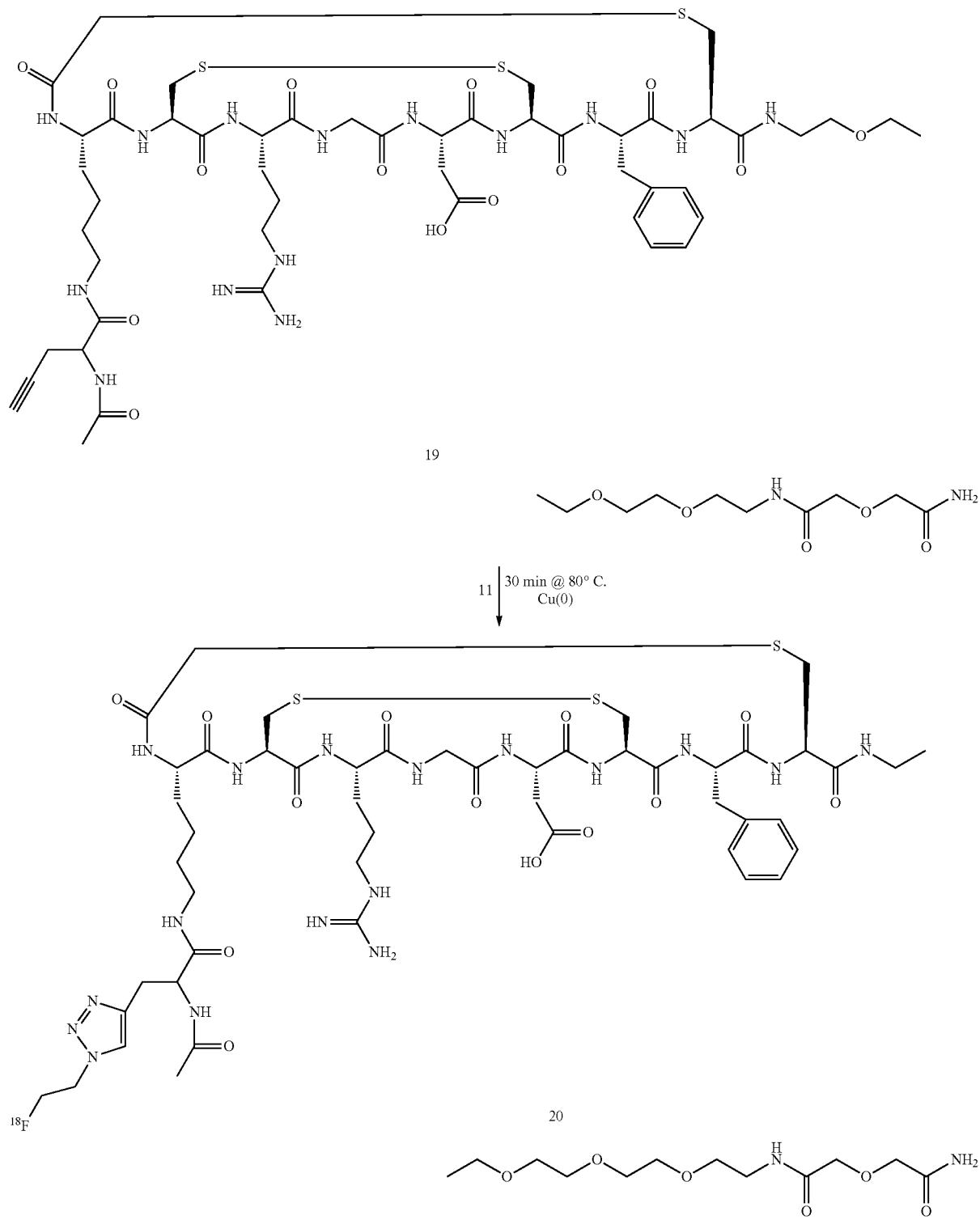

(i) Preparation of Compound 19

Cys2-6; c[CH$_2$CO-Lys(DL-Pra-Ac)-Cys-Arg-Gly-Asp-Cys-Phe-Cys]-CCX6-NH$_2$

Ac-DL-Pra-OH (31 mg), (7-Azabenzotriazole-1-yloxy)tripyrrolidinophosphonium hexafluorophosphate (PyAOP) (104 mg) and N-methylmorpholine (NMM) (88 µL) were dissolved in dimethylformamide (DMF) (3 mL) and the mixture stirred for 5 minutes prior to addition of ClCH$_2$CO-Lys-Cys(tBu)-Arg-Gly-Asp-Cys(tBu)-Phe-Cys-PEG-NH$_2$ (126 mg) prepared as described in WO2005/003166 dissolved in DMF (4 mL). The reaction mixture was stirred for 45 minutes. More ClCH$_2$CO-Lys-Cys(tBu)-Arg-Gly-Asp-Cys(tBu)-Phe-Cys-PEG-NH$_2$ (132 mg) and NMM (44 µL) were added and stirring continued for 45 minutes. DMF was then evaporated in vacuo, the residue (5 mL) diluted with 10% acetonitrile (ACN)/water (100 mL) and the product purified using preparative HPLC.

Purification and Characterisation

Purification by preparative HPLC (gradient: 10-40% B over 60 min where A=H$_2$O/0.1% TFA and B=ACN/0.1% TFA, flow rate: 50 mL/min, column: Phenomenex Luna 5µ C18 (2) 250×50 mm, detection: UV 214 nm, product retention time: 31.3 min) of the diluted residue afforded 170 mg pure AH-112145.

The pure product was analysed by analytical HPLC (gradient: 10-40% B over 10 min where A=H$_2$O/0.1% TFA and B=ACN/0.1% TFA, flow rate: 0.3 mL/min, column: Phenomenex Luna 3µ C18 (2) 50×2 mm, detection: UV 214 nm, product retention time: 6.32 min). Further product characterisation was carried out using electrospray mass spectrometry (MH$^+$ calculated: 1395.5, MH$^+$ found: 1395.7).

(ii) Preparation of Compound 20

Compound (19) (0.5 mg, 0.35 µmol) was dissolved in sodium phosphate buffer (pH 6.0, 50 mM) and mixed with a solution of compound (11) (25 µl, 728 µCi/25 MBq) and copper powder (200 mg, 40 mesh). After heating for 15 minutes at 70° C., the mixture is analysed by radio HPLC.

The conjugation product (20) was isolated using semi-preparative HPLC (column Luna C18(2), 100×10 mm, flow rate 2.0 ml/min; solvent A: water (0.085% phosphoric acid v/v), solvent B: water (30% ethanol v/v), gradient: 50% B to 100% B in 15 minutes. The labelled peptide (20) was obtained with a decay-corrected radiochemical yield of 10% and a radiochemical purity of >99%. The identity of the radioactive product peak (k'=2.03) was confirmed by co-injection with a standard sample of compound (20).

Example 13

Optimization of Reaction Parameters for the Preparation of Compound (20)

General Procedure:

To a solution of compound (19) (0.5 mg, 0.35 µmol) in buffer (50 µl; buffer A: sodium phosphate, pH 6.0, 50 mM; buffer B: sodium carbonate, pH 9.3, 50 mM) is added compound (11) (0.1 mCi, 3.7 MBq) in acetonitrile (100 µl), followed by copper catalyst (catalyst 1: copper granules 10+40 mesh, catalyst 2: copper powder –40 mesh, catalyst 3: copper powder, dendritic, 3 µm). The mixture was incubated for 15 minutes at 80° C. and analyzed by HPLC.

TABLE 2

Labelling efficiency of compound (19) to form compound (20) depending on pH and catalyst (400 mg) as measured by HPLC

| Buffer | Catalyst 1 | Catalyst 2 | Catalyst 3 |
|--------|------------|------------|------------|
| A | 12% | 44% | —* |
| B | — | 33% | —* |

*no UV peak for peptide precursor found

TABLE 3

Labelling efficiency of compound (19) to form compound (20) depending amount of catalyst 3 at pH 6.0 (buffer A).

| Amount of catalyst 3 | Labelling efficiency of compound (20) |
|---|---|
| 200 mg | 23% |
| 100 mg | 37% |
| 50 mg | 27% |

The invention described and claimed herein is not to be limited in scope by the specific embodiments herein disclosed, since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A compound of formula (V) or (VI):

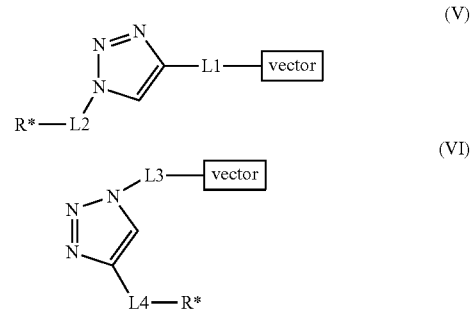

wherein

L1, L2, L3, and L4 are each independently a C$_{1-60}$ hydrocarbyl group optionally including 1 to 30 heteroatoms, which is optionally substituted with one or more groups selected from ether, thiooether, sulphonamide, amide, amino acid, carbohydrate, or monomers and polymers comprising ethyleneglycol;

R* is a reporter moiety selected from the group consisting of radionuclides and radionuclides incorporated into a chelating agent wherein said chelating agent is a chelating agent of Formula X:

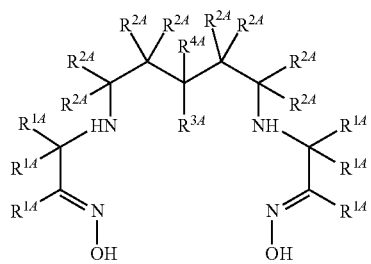

(X)

where:
each $R^{1A}$, $R^{2A}$, $R^{3A}$ and $R^{4A}$ is independently an $R^A$ group;
each $R^A$ group is independently H or $C_{1-10}$ alkyl, $C_{3-10}$ alkylaryl, $C_{2-10}$ alkoxyalkyl, $C_{1-10}$ hydroxyalkyl, $C_{1-10}$ alkylamine, $C_{1-10}$ fluoroalkyl, or 2 or more $R^A$ groups, together with the atoms to which they are attached form a carbocyclic, heterocyclic, saturated or unsaturated ring; and
vector is a peptide, protein, hormone, cell, bacterium, or virus.

2. A compound of formula (V) or (VI) according to claim 1 wherein the vector is Arg-Gly-Asp peptide.

3. A compound of formula (V) or (VI) according to claim 1 wherein the vector is a peptide comprising the fragment:

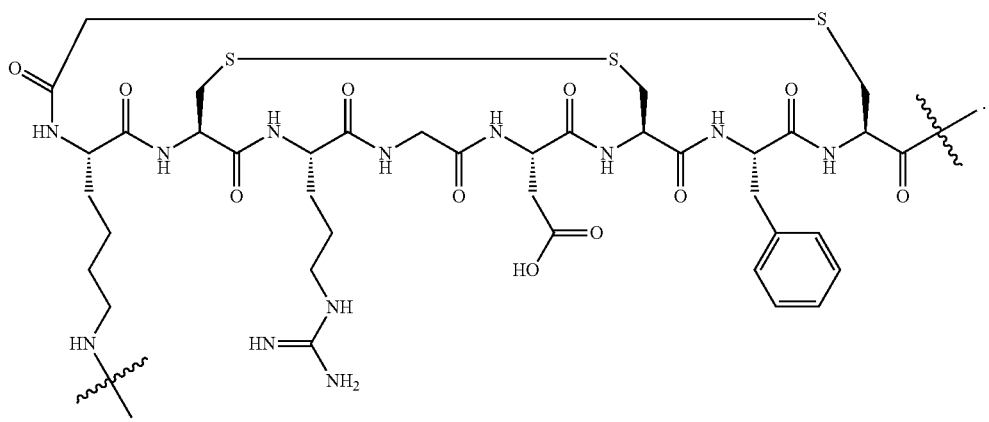 [SMILES: *NCCCC[C@@H]1NC(=O)CSC[C@@H](C(*)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]

4. A radiopharmaceutical composition comprising an effective amount of a compound according to claim 1 together with one or more pharmaceutically acceptable adjuvant, excipient or diluent.

5. A compound of formula (V) or (VI) according to claim 1 wherein the vector is a peptide of formula (A):

wherein $X^7$ is either —$NH_2$ or

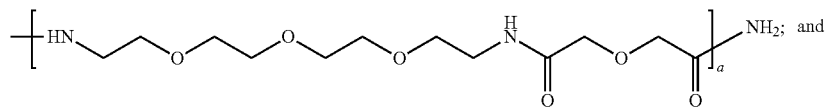

wherein a is an integer of from 1 to 10.

6. A compound of formula (V) or (VI) according to claim 5 wherein a is 1.

7. A radiopharmaceutical composition comprising an effective amount of a compound according to claim 2 together with one or more pharmaceutically acceptable adjuvant, excipient or diluent.

8. A radiopharmaceutical composition comprising an effective amount of a compound according to claim 3 together with one or more pharmaceutically acceptable adjuvant, excipient or diluent.

9. A compound according to claim 1, wherein said $C_{1-60}$ hydrocarbyl group optionally including 1 to 30 heteroatoms is an alkyl, alkenyl, alkynyl, aromatic, polyaromatic, or heteroaromatic group.

* * * * *